United States Patent [19]
Williams

[11] Patent Number: 5,897,585
[45] Date of Patent: Apr. 27, 1999

[54] STRETCHABLE PACING LEAD

[75] Inventor: Terrell M. Williams, Brooklyn Park, Minn.

[73] Assignee: Medtronic, Inc., Minneapolis, Minn.

[21] Appl. No.: 08/993,084

[22] Filed: Dec. 18, 1997

[51] Int. Cl.$^6$ .................................................. A61N 1/05
[52] U.S. Cl. ............................................................. 607/122
[58] Field of Search ...................... 607/122, 116, 607/127, 128, 119, 123, 126, 137, 129; 600/372, 373–375, 377, 379

[56] References Cited

U.S. PATENT DOCUMENTS

| | | |
|---|---|---|
| 2,913,587 | 11/1959 | Gebhard . |
| 3,844,292 | 10/1974 | Bolduc . |
| 3,902,501 | 9/1975 | Citron et al. . |
| 4,013,081 | 3/1977 | Kolenik . |
| 4,106,512 | 8/1978 | Bisping . |
| 4,217,913 | 8/1980 | Dutcher . |
| 4,282,886 | 8/1981 | King . |
| 4,402,323 | 9/1983 | White . |
| 4,424,818 | 1/1984 | Doring et al. . |
| 4,479,500 | 10/1984 | Smits ...................................... 607/123 |
| 4,574,814 | 3/1986 | Buffet ...................................... 607/123 |
| 4,662,382 | 5/1987 | Sluetz et al. ............................ 607/126 |
| 4,964,414 | 10/1990 | Handa et al. . |
| 5,092,333 | 3/1992 | Tsuchida et al. ........................ 607/122 |
| 5,246,014 | 9/1993 | Williams et al. . |
| 5,324,321 | 6/1994 | Pohndorf et al. ........................ 607/116 |
| 5,466,255 | 11/1995 | Franchi ................................... 607/128 |
| 5,578,067 | 11/1996 | Ekwall et al. ........................... 607/122 |
| 5,658,327 | 8/1997 | Altman et al. ........................... 607/127 |

FOREIGN PATENT DOCUMENTS 004667  10/1979  European Pat. Off. .

OTHER PUBLICATIONS

"Evaluation of Expandable Leadwires for Pediatric Cochlear Implants", Xu et al, Amer. Jnl. Otology/ vol.14, No.2, Mar. 1993.

Primary Examiner—William E. Kamm
Assistant Examiner—Kennedy J. Schaetzle
Attorney, Agent, or Firm—Reed A. Duthler; Harold R. Patton

[57] ABSTRACT

An implantable electrical lead having a lead body fabricated of a first, inner tube and a second, outer tube, the first, inner tube, mounted slideably within the outer tube, the outer tube overlapping the inner tube along at least a portion of its length; and having a conductor extendible along a portion of its length, mounted within and extending along the first and second tubes with the extendible portion of the conductor extending within a region in which the outer tube overlaps the inner tube and having an electrode mounted to a distal portion of the lead body, coupled to the conductor. The inner and outer tubes are preferably approximately the same length, and the extendible portion of the conductor preferably extends along a majority of its length. The extendible conductor may be a coiled conductor provided with an insulative coating.

25 Claims, 3 Drawing Sheets

STRETCHABLE PACING LEAD

BACKGROUND OF THE INVENTION

The present invention relates to medical electrical leads generally and more particular to cardiac pacing and defibrillation leads.

When a cardiac pacemaker is implanted into a pediatric patient, the distal end of the lead carrying the electrode is anchored with respect to the heart and the proximal end of the lead is anchored to or near the pacemaker. As the patient grows, the distance between the pacemaker and the electrode at the distal end of the lead generally increases. It has long been recognized that it would be desirable to provide a mechanism to deal with this phenomenon. One proposed mechanism is to provide a sheath around the pacemaker in which the lead may loosely be looped, so that it may be pulled out of the sheath as the patient grows. This approach is disclosed in U.S. Pat. No. 4,013,081 issued to Kolenik.

An alternative approach is to provide a capsule or envelope in which the lead body may be loosely coiled or folded, allowing the lead body to be pulled from the capsule or envelope as the patient grows. This approach is disclosed in U.S. Pat. No. 4,913,587. A third approach is to provide a lead having a lead body which may be elongated, and a conductor therein which permits for some degree of stretch. One such lead is disclosed in European Patent application EP 0004667, in which the lead body is folded back upon itself to provide a concertina-type fold allowing for elongation of the lead body. In this lead, several such concertina folds are provided spaced along the length of the lead to allow for expansion at multiple individual locations along the lead.

In the context of leads employed in cochlear implants, as described in the article, Evaluation of Expandable Lead Wires for Pediatric Cochlear Implants, by ShiAng Xu et al, published in the American Journal of Otology, Vol. 14, No. 2, March, 1993, pages 151–160, an additional mechanism is proposed in which a generally straight, stranded conductor is coiled over a portion of its length and enveloped in an outer tube as a substitute for an envelope or enclosure.

SUMMARY OF THE INVENTION

The present invention is directed toward providing a workable expandable pacing lead which allows for extension of the lead body length as the patient grows. The present invention accomplishes this goal by means of a lead which has a lead body fabricated of at least two overlapping tubes which are freely slideable with respect to one another. Mounted within the tube is an elongated conductor which is configured to be extendible over that portion of its length extending through the overlapping portions of the two tubes. Preferably the conductor is configured to allow for an increase in length in the vicinity of 2X, and the corresponding inner and outer tubes of which the lead body is fabricated are correspondingly dimensioned, so that if two overlapping tubes are employed, when the lead exhibits its shortest length, the inner tube extends substantially to the proximal end of the outer tube, and the outer tube extends substantially to the distal end of the inner tube. The substantial overlap of the tubes, especially when the lead is initially implanted, prevents fibrotic tissue ingrowth into the conductor which might otherwise interfere with later elongation of the conductor.

DETAILED DESCRIPTION OF THE PREFERRED EMBODIMENT

Figure 1:
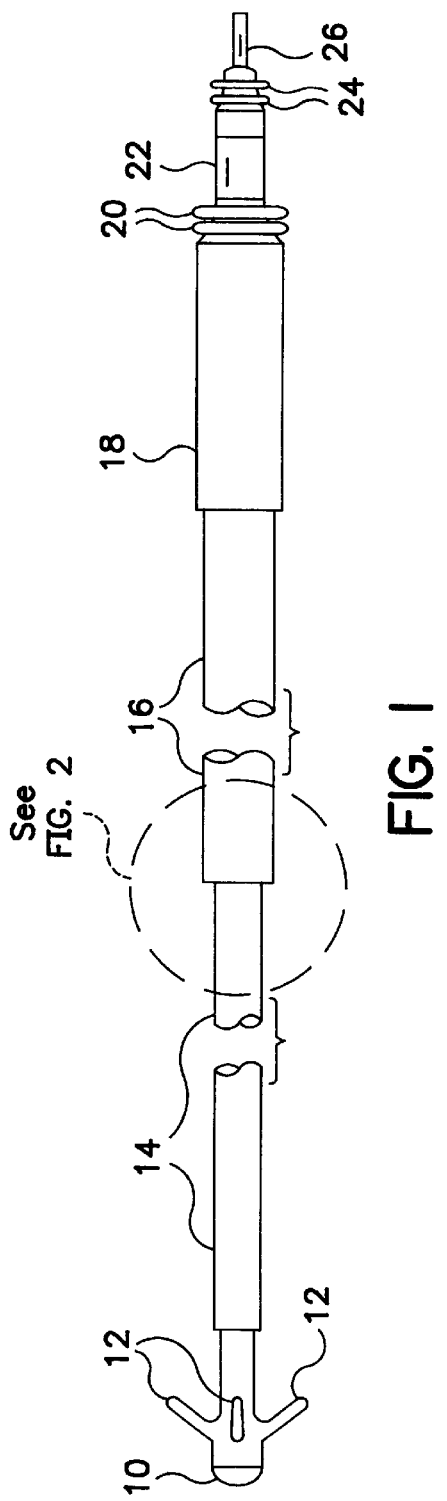
FIG. 1 is a plan view of the lead according to the present invention.

FIG. 1 is a plan view of an endocardial lead employing the present invention. At the distal end of the lead is pacing electrode 10, and associated pliant tines 12 as described in U.S. Pat. No. 3,902,501 issued to Citron et al. Alternatively, an active fixation mechanism as described in U.S. Pat. No. 4,106,512 issued to Bisping or U.S. Pat. No. 4,217,913 issued to Dutcher, both incorporated by reference in their entireties, might be substituted for electrode 10 and tines 12. If the invention is practiced in the form of an epicardial lead, an epicardial or myocardial electrode as disclosed in U.S. Pat. No. 4,402,323 issued to White, U.S. Pat. No. 4,424,818 issued to Doring et al. or U.S. Pat. No. 4,282,886 issued to King, all incorporated by reference herein in their entireties may be substituted. Generally, the present invention is believed to be useful in conjunction with endocardial, epicardial, or myocardial electrodes of any known type.

Extending proximally from electrode 10 and tines 12 is the first or inner tube 14 of the lead body. Inner tube 14 extends proximally into the outer or second tube 16 which in turn extends proximally to connector assembly 18. Connector assembly 18 carries a connector ring 22 and a connector pin 26, and is provided with sealing rings 20 and 24. Connector assembly 18 generally takes the form of an IS-1 compatible connector. In the specific embodiment illustrated, connector pin 26 is coupled to pacing electrode 10. In other embodiments, connector ring 22 might be coupled to an additional electrode or a sensor.

The conductor within inner and outer tubes 14 and 16 is fabricated so that it may display an increase in diameter along a portion of its length which extends within the overlap of inner and outer tubes 14 and 16. Inner and outer tubes 14 and 16 may be approximately the same length, so that when the lead is in its shortest configuration, the distal ends of inner and outer tubes 16 and 14 are relatively closely adjacent, as are their proximal ends. When fully extended, the proximal end of inner tube 14 should still be within inner tube 16, but more closely adjacent to the distal end of outer tube 16. In the context of a device employing the present invention using two nested tubes as illustrated, this allows for the lead to be almost doubled in length by movement of inner tube 14 distally with respect to outer tube 16.

Figure 2:
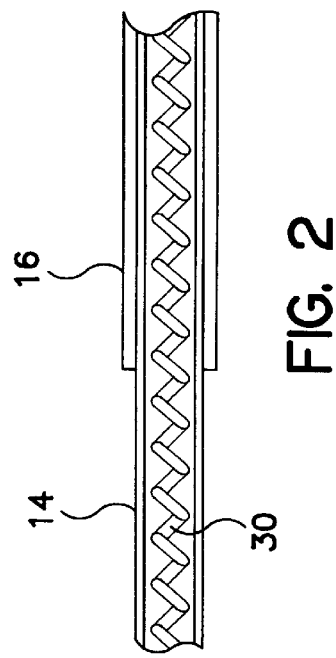
FIG. 2 is a cross-sectional view through a portion of the lead of FIG. 1.

FIG. 2 illustrates a cross-sectional view through the lead of FIG. 1 at the point at which inner tube 14 exits the distal end of outer tube 16. In this view, the stretchable conductor 30 is illustrated. Stretchable conductor 30 may be, for example, a bundled or stranded wire wound into a coil and coated with an insulative material as disclosed in U.S. Pat. No. 4,964,414 issued to Handa et al, incorporated herein in its entirety. Alternatively, the conductor may be a cabled conductor as disclosed in U.S. Pat. No. 5,246,014 issued to Williams et al., also incorporated herein in its entirety, provided with an insulative plastic coating and wound into a coiled configuration. Alternatively, the lead might take the form of tinsel wire as disclosed in U.S. Pat. No. 3,844,292 issued to Bolduc and incorporated herein by reference in its entirety, correspondingly insulated with a plastic coating and wound into a coiled configuration. Thermoplastics such as flouroelastomers, polyurethanes or polyethylenes are particularly preferred for the insulative coating of conductor 30, as this allows for winding of the coated conductor around a mandrel, followed by heat setting in order to retain the coiled configuration.

Inner and outer sheaths 14 and 16 are preferably fabricated of a material which is minimally thrombogenic and has a relatively low friction of coefficient, allowing the inner and outer tubes 14 and 16 to readily slide with respect to one another. For example, the inner and outer tubes 14 and 16 may be fabricated of a thin flouropolymer such as PTFE, of a polyurethane such as presently employed in cardiac pacing leads or of other similar material.

Preferably, the length over which conductor 30 is coiled extends as far as possible along the length of the lead body whereby the area of elongation of the conductor is distributed as much as possible along the length of the lead, facilitating substantial elongation without adversely affecting the flex life of the conductor. In the case of the lead illustrated in FIG. 1, it may be necessary to include relatively shorter straight sections of the conductor 30 at the proximal end distal ends in the vicinity of electrode IO and connector assembly 18.

Figure 3:
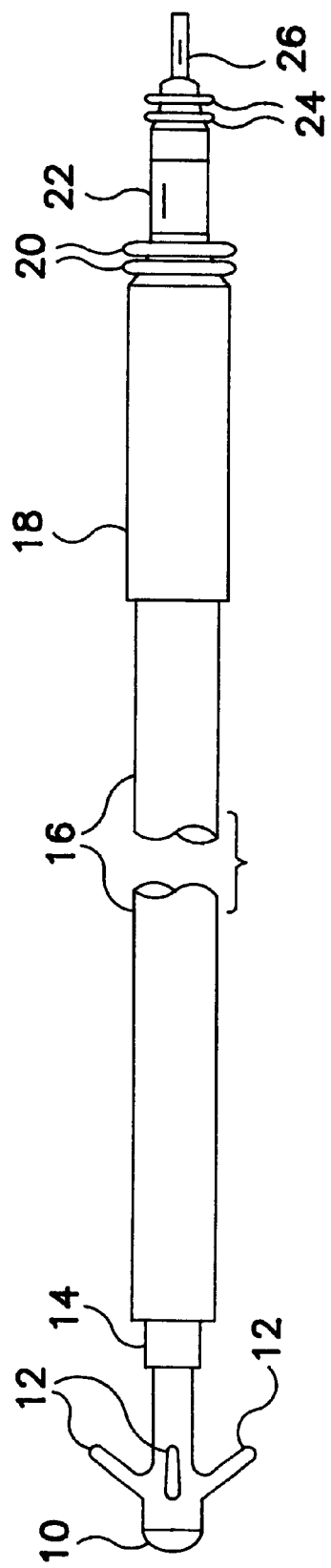
FIG. 3 is a plan view of a lead according to the present invention, in a configuration exhibiting its shortest length.

FIG. 3 illustrates the lead of FIG. 1 in its shortest configuration. All numbered components correspond top identically numbered components in FIG. 1. In this configuration, because the lengths of tubes 14 and 16 are approximately the same, the outer tube 16 extends substantially to the distal end of the inner tube 18 and correspondingly the inner tube 14 extends substantially to the proximal end of the outer tube 16.

Figure 4:
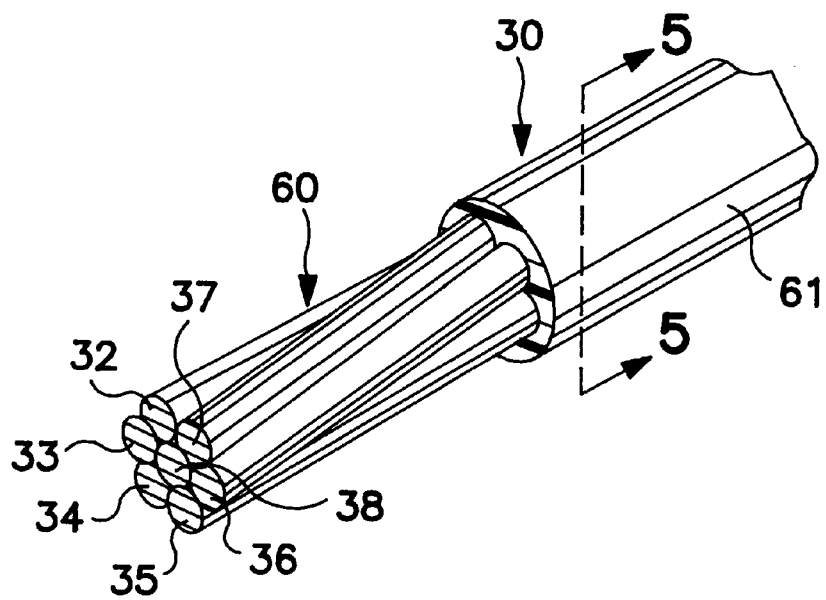
FIG. 4 is a cutaway view of an insulated conductor appropriate for use in conjunction with the present invention.

FIG. 4 illustrates the insulated conductor 30 in a cut-away view. The insulated conductor comprises a stranded conductor 60 and a protective insulation coating 61. The stranded conductor 60 includes the strands 32–38 which are made of electrically conductive filaments. In the preferred embodiment, the conductor 60 is composed of six peripheral strands 32–37 which are arranged around a central strand 38. It should however be understood that a different number of strands can be used to form the stranded conductor 60 of the present invention.

The strands 32–38 are stranded together using a conventional stranding machine to cause them to be tightly bundled in a cable-like fashion to form the conductor 60. The strands 32–38 are made of a biocompatible and biostable electrically conductive material such as MP35N, or other material that is fatigue and corrosion resistant. To enhance fluoroscopic visibility, a high density material, such as platinum or platinum alloys, may be used.

The coating 61 is made of dielectric fluoropolymer material which is biocompatible, biostable, resistant to abrasion, flexible and tough. As illustrated in FIG. 3, the coating 61 is formed over the conductor 60 in an even manner for producing a smooth outer surface of a generally circular outer diameter.

Figure 5:
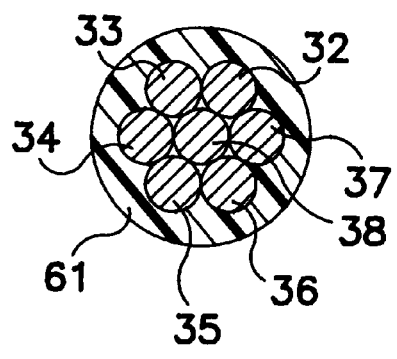
FIG. 5 is a cross-sectional view through the insulated conductor of FIG. 4.

Referring now to FIG. 5, there is illustrated a cross-sectional view of the preferred embodiment of the insulated conductor 30 taken along line 5—5 in FIG. 3. The insulation coating 61 is formed tightly around the conductor 60 and the conductor 60 is centered at about the geometric axis of symmetry of the insulation coating 61, in order to obtain maximum insulation characteristics around the entire stranded conductor 60.

Figure 6:
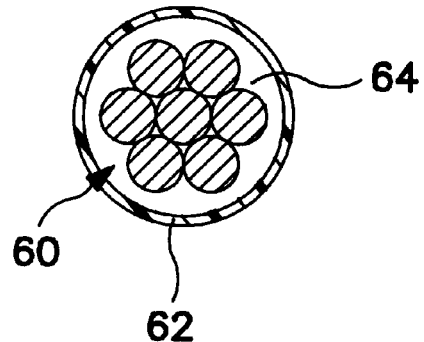
FIG. 6 is a cross-sectional view through an alternative embodiment of an insulated conductor appropriate for use with the present invention.

FIG. 6 is a cross sectional view of an alternative embodiment of the insulated conductor 30, having a conductor 60, and an insulation tubing 62 which surrounds the conductor 60 in a loose manner, with a spatial gap 64 formed in between.

One advantage of this alternative embodiment is to reduce the corrosion resulting from a pin hole leak. If a pin hole were to develop in the tubing 62, the body fluid will leak through the tubing 62 inside the spatial gap 64. The leaking fluid will flow within the gap 64, to reduce the current density at the surface of the conductor 60, and to dilute the corrosive pH concentration on the surface of the conductor 60, thus substantially reducing corrosion.

In conjunction with the above disclosure, I claim:

1. An implantable electrical lead extendible from a first, shorter configuration to a second longer configuration, comprising:

a lead body with proximal and distal ends, having an electrode mounted at the distal end of the lead body and a connector assembly mounted at the proximal end of the lead body, wherein the lead body comprises a first, inner tube having proximal and distal ends and a second, outer tube having proximal and distal ends, the first, inner tube, mounted slideably within the outer tube, one of the first and second tubes extending from the connector assembly to a point distal thereto, the other of the first and second tubes extending from the electrode to a point proximal thereto, the outer tube overlapping the inner tube along its length in the first configuration such that the second tube extends substantially to the distal end of the first tube; and a conductor coupled to the connector assembly and the electrode and extendible along a portion of its length, mounted within and extending along the first and second tubes such that said extendible portion of said conductor extends within a region in which said outer tube overlaps said inner tube.

2. A lead according to claim 1 wherein the extendible portion of said conductor extends along a majority of its length.

3. A lead according to claim 1 or claim 2 wherein said extendible conductor is provided with an insulative coating.

4. A lead according to claim 1 or claim 2 wherein said conductor is a coiled conductor.

5. A lead according to claim 1 or claim 2 wherein said conductor is a stranded conductor provided with outer insulation and wound into a coil.

6. An implant able electrical lead extendible from a first, shorter configuration to a second longer configuration, comprising:

a lead body with proximal and distal ends, having an electrode mounted at the distal end of the lead body and a connector mounted at the proximal end of the lead body, wherein the lead body comprises a first, inner tube having proximal and distal ends and a second, outer tube having proximal and distal ends, the first, inner tube, mounted slideably within the outer tube to allow extension of the lead from the first configuration to the second configuration, the first and second tubes sized such that the second configuration has a length approximately twice the length of the first configuration; and a conductor coupled to the connector assembly and the electrode and extendible along a portion of its length, mounted within and extending along the first and second tubes such that the extendible portion of the conductor extends within a region in which the outer tube overlaps the inner tube.

7. A lead according to claim 6 wherein the extendible portion of the conductor extends along a majority of its length.

8. A lead according to claim 6 wherein the lengths of the first and second tubes are approximately equal.

9. A lead according to claim 6 or claim 7 or claim 8 wherein the conductor is provided with an insulative coating.

10. A lead according to claim 6 or claim 7 or claim 8 wherein the conductor is a coiled conductor.

11. A lead according to claim 6 or claim 7 or claim 8 wherein the conductor is a stranded conductor provided with outer insulation and wound into a coil.

12. An implant able electrical lead extendible from a first, shorter configuration to a second longer configuration, comprising:

a lead body with proximal and distal ends, having an electrode mounted at the distal end of the lead body and a connector mounted at the proximal end of the lead body and extending means for allowing the lead body to extend while implanted in a patient's body, wherein the extending means comprises a first, inner tube and a second, outer tube overlapping the inner tube, the first, inner tube, slideable within the outer tube after implant to allow extension of the lead from the first configuration to the second configuration after implant; and a conductor coupled to the connector assembly and the electrode and extendible along a portion of its length, mounted within and extending along the first and second tubes such that the extendible portion of the conductor extends within a region in which the outer tube overlaps the inner tube.

13. A lead according to claim 12 wherein the extendible portion of the conductor extends along a majority of its length.

14. A lead according to claim 12 wherein the lengths of the first and second tubes are the first and second tubes sized such that the second configuration has a length approximately twice the length of the first configuration; approximately equal.

15. A lead according to claim 12 wherein the first and second tubes sized such that the second configuration has a length approximately twice the length of the first configuration.

16. A lead according to claim 12 or claim 13 or claim 14 or claim 15 wherein the extendible conductor is provided with an insulative coating.

17. A lead according to claim 12 or claim 13 or claim 14 or claim 15 wherein the conductor is a coiled conductor.

18. A lead according to claim 12 or claim 13 or claim 14 or claim 15 wherein the conductor is a stranded conductor provided with outer insulation and wound into a coil.

19. An implantable electrical lead extendible from a first, shorter configuration to a second longer configuration, comprising:

a lead body with proximal and distal ends, having an electrode mounted at the distal end of the lead body and a connector mounted at the proximal end of the lead body and extending means for allowing the lead body to extend while implanted in a patient's body, wherein the extending means comprises a first, inner tube and a second, outer tube overlapping the inner tube, the first, inner tube not mechanically interlocked to the first tube and slideable within the outer tube after implant to allow extension of the lead from the first configuration to the second configuration while implanted; and a conductor coupled to the connector assembly and the electrode and extendible along a portion of its length, mounted within and extending along the first and second tubes such that the extendible portion of the conductor extends within a region in which the outer tube overlaps the inner tube.

20. A lead according to claim 19 wherein the extendible portion of the conductor extends along a majority of its length.

21. A lead according to claim 19 wherein the lengths of the first and second tubes are approximately equal.

22. A lead according to claim 19 wherein the first and second tubes are sized such that the second configuration has a length approximately twice the length of the first configuration.

23. A lead according to claim 19 or claim 20 or claim 21 or claim 22 wherein the extendible conductor is provided with an insulative coating.

24. A lead according to claim 19 or claim 20 or claim 21 or claim 22 wherein the conductor is a coiled conductor.

25. A lead according to claim 19 or claim 20 or claim 21 or claim 22 wherein the conductor is a stranded conductor provided with outer insulation and wound into a coil.

* * * * *